United States Patent [19]

Duffett

[11] Patent Number: Plant 5,502

[45] Date of Patent: Jun. 25, 1985

[54] CHRYSANTHEMUM PLANT NAMED CHARM

[75] Inventor: William E. Duffett, Salinas, Calif.

[73] Assignee: Yoder Brothers, Inc., Barberton, Ohio

[21] Appl. No.: 506,505

[22] Filed: Jun. 21, 1983

[51] Int. Cl.[3] ..... A01H 5/00

[52] U.S. Cl. ..... Plt./76

[58] Field of Search ..... Plt./76, 80

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant named Charm having flat capitulum form; decorative capitulum type; light lavender pink ray floret color; diameter across face of capitulum ranging from 90 to 110 mm. at maturity; uniform eight week photoperiodic flowering response to short days; medium plant height when grown as a pinched disbudded pot mum; and spreading branching pattern.

3 Drawing Figures

The present invention comprises a new and distinct cultivar of *Chrysanthemum morifolium,* Ramat., named Charm.

Charm is a product of a planned breeding program which had the objective of creating new chrysanthemum cultivars for pinched, disbudded pot mum programs having decorative capitulum type, lavender floret color, eight or nine week photoperiodic flowering response, and having the ability to produce commercially acceptable quality in year round programs. Such traits in combination were not present or needed improvement in previously available commercial cultivars.

Charm was originated from a cross made in a controlled breeding program in Salinas, Calif. in 1979. The female parent was Tempo, disclosed in U.S. Plant Pat. No. 4,505, originated by the present inventor from a hybridization of two unnamed pink decorative seedlings. The male parent of Charm was identified as 775052, originated from a cross between Cymbals, disclosed in pending Application for U.S. Plant Pat. Ser. No. 313,274, and an unnamed yellow daisy 752181.

Charm was discovered and selected as one flowering plant within the progeny of the stated cross by William E. Duffett on May 9, 1980 in a controlled environment in Salinas, Calif.

The first act of asexual reproduction of Charm was accomplished when vegetative cuttings were taken from the initial selection in August 1980 in a controlled environment in Salinas, Calif. by a technician working under formulations established and supervised by William E. Duffett. Horticultural examination of selected units initiated July 15, 1981 has demonstrated that the combination of characteristics as herein disclosed for Charm are firmly fixed and retained through successive generations of asexual reproduction.

Charm has not been observed under all possible environmental conditions. The phenotype may vary significantly with variations in environment such as temperature, light intensity and day length. The observations, measurements and comparisons describe plants grown in Salinas, Calif. and Leamington, Canada under greenhouse conditions which approximate those generally used in commercial practice.

The following traits have been repeatedly observed and are determined to be basic characteristics of Charm which in combination distinguish this chrysanthemum as a new and distinct cultivar:

(1) Flat capitulum form;

(2) Decorative capitulum type;

(3) Light lavender pink ray floret color;

(4) Diameter across face of capitulum ranging from 90 to 110 mm. at maturity;

(5) Uniform eight week photoperiodic flowering response to short days;

(6) Medium plant height, requiring 2 long day weeks prior to pinch and short days, and 1–2 applications of 2500 ppm B-9 14 to 21 days after the beginning of short days to attain a flowered plant height of 30 to 35 cm.; and (7) Spreading branching pattern.

The accompanying photographic drawings depict typical foliage and inflorescence characteristics of Charm. Sheet 1 is a color photograph of a plant of Charm grown as a pinched isbudded pot mum, with colors being as accurate as possible with renditions of this type. Sheet 2 is a black and white photograph of three views of the inflorescence of Charm. Sheet 3 shows the leaves of Charm in three stages of development (mature, intermediate, immature).

Of the many commercial cultivars known to the present inventor, the most similar in comparison to Charm is the commercially available cultivar Always Pink, disclosed in U.S. Plant Pat. No. 3,256. Reference is made to attached Chart A which compares certain characteristics of Charm to those same characteristics of Always Pink.

Charm is similar to Always Pink in flowering response period and capitulum form and type. However, the flower form of Charm normally remains flat with maturity. Always Pink reflexes at maturity with diminished keeping quality.

Charm displays a more spreading branching pattern, a larger diameter across the face of the capitulum and a more vigorous plant habit.

The color of Charm is lighter than Always Pink. It is practically resistant to color oxidation whereas Always Pink oxidizes rapidly.

In the following description, color references are made to The Royal Horticultural Society Colour Chart. The color values were determined between 11:00 A.M. and 12:00 P.M. on Dec. 9, 1982 under 150 foot-candle light intensity at Salinas, Calif.

Classification:

*Botanical.*—*Chrysanthemum morifolium,* Ramat., cv CHARM.

*Commercial.*—Disbud decorative pot mum.

INFLORESCENCE

A. Capitulum:

*Form.*—Flat.

*Type.*—Decorative.

*Diameter across face.*—90 to 110 mm.

B. Corolla of ray florets:

*Color (general tonality from a distance of three meters).*—Light lavender pink.

*Color (abaxial).*—75A-C.

*Color (adaxial).*—76B-C.

*Shape.*—Flat, oblong.

C. Corolla of disc florets:

*Color (mature).*—154B.

*Color (immature).*—149B.

D. Reproductive organs:

*Androecium.*—Present disc florets only; scant pollen.

*Gynoecium.*—Present both ray and disc florets.

PLANT

A. General appearance:

*Height.*—Medium; 30 to 35 cm. given 2 long day weeks before pinch and lights out, and 1-2 applications of 2500 ppm B-9 SP after lights out.

*Branching pattern.*—Spreading.

B. Foliage:

*Color (abaxial).*—147B.

*Color (adaxial).*—158B.

*Shape.*—Moderately lobed. Deeply serrated.

CHART A

COMPARISON OF CHARM AND ALWAYS PINK

| CULTIVAR | RAY FLORET COLOR | CAPITULUM FORM AND TYPE | BRANCHING PATTERN |
|---|---|---|---|
| CHARM | LIGHT LAVENDER PINK | FLAT DECORATIVE | SPREADING |
| ALWAYS PINK | LAVENDER PINK | FLAT DECORATIVE | UPRIGHT |

| CULTIVAR | DIAMETER ACROSS FACE OF CAPITULUM | PLANT HEIGHT | FLOWERING RESPONSE PERIOD |
|---|---|---|---|
| CHARM | 90 to 110 mm. | MEDIUM 30 to 35 cm. | 8 WEEK |
| ALWAYS PINK | 80 to 100 mm. | SHORT 25 to 30 cm. | 8 WEEK |

COMPARISONS MADE OF PLANTS GROWN AS PINCHED DISBUDDED POT MUMS SALINAS, CALIFORNIA AND LEAMINGTON, CANADA

I claim:

1. A new and distinct cultivar of *Chrysanthemum morifolium,* Ramat., named Charm, as described and illustrated, and particularly characterized as to uniqueness by the combined characteristics of flat capitulum form; decorative capitulum type; light lavender pink ray floret color; diameter across face of capitulum ranging from 90 to 110 mm. at maturity; uniform eight week photoperiodic flowering response; medium plant height, and spreading branching pattern.

* * * * *

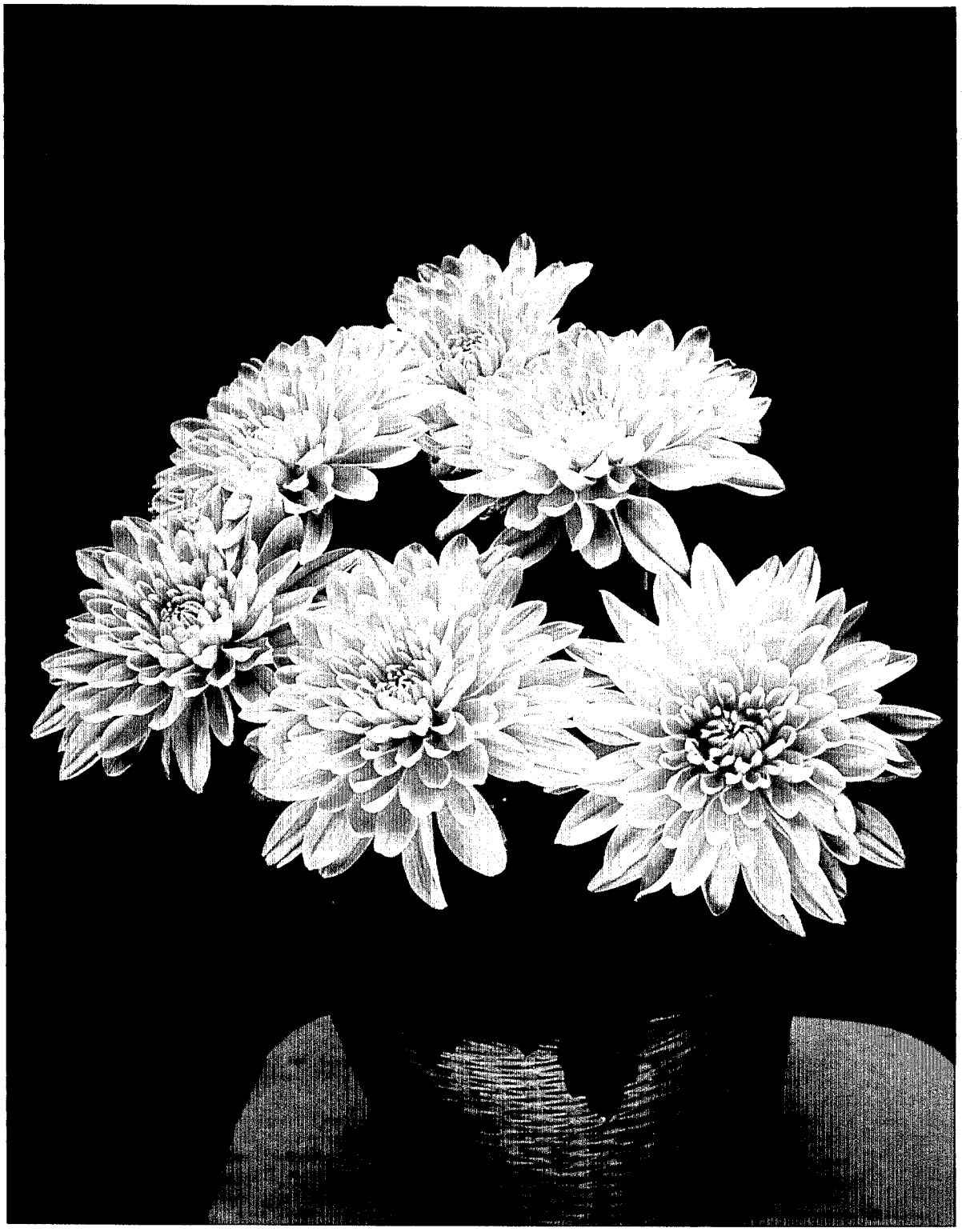

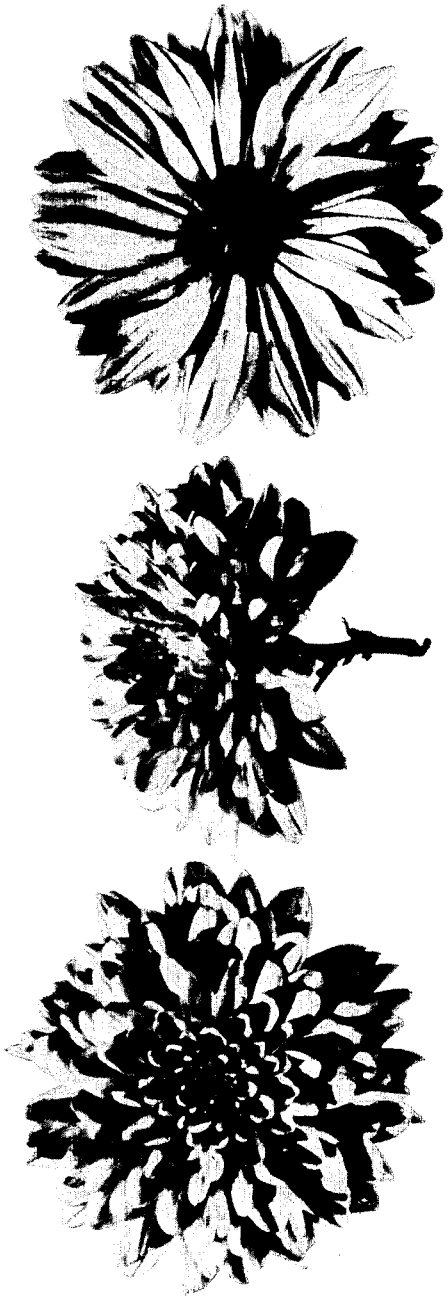

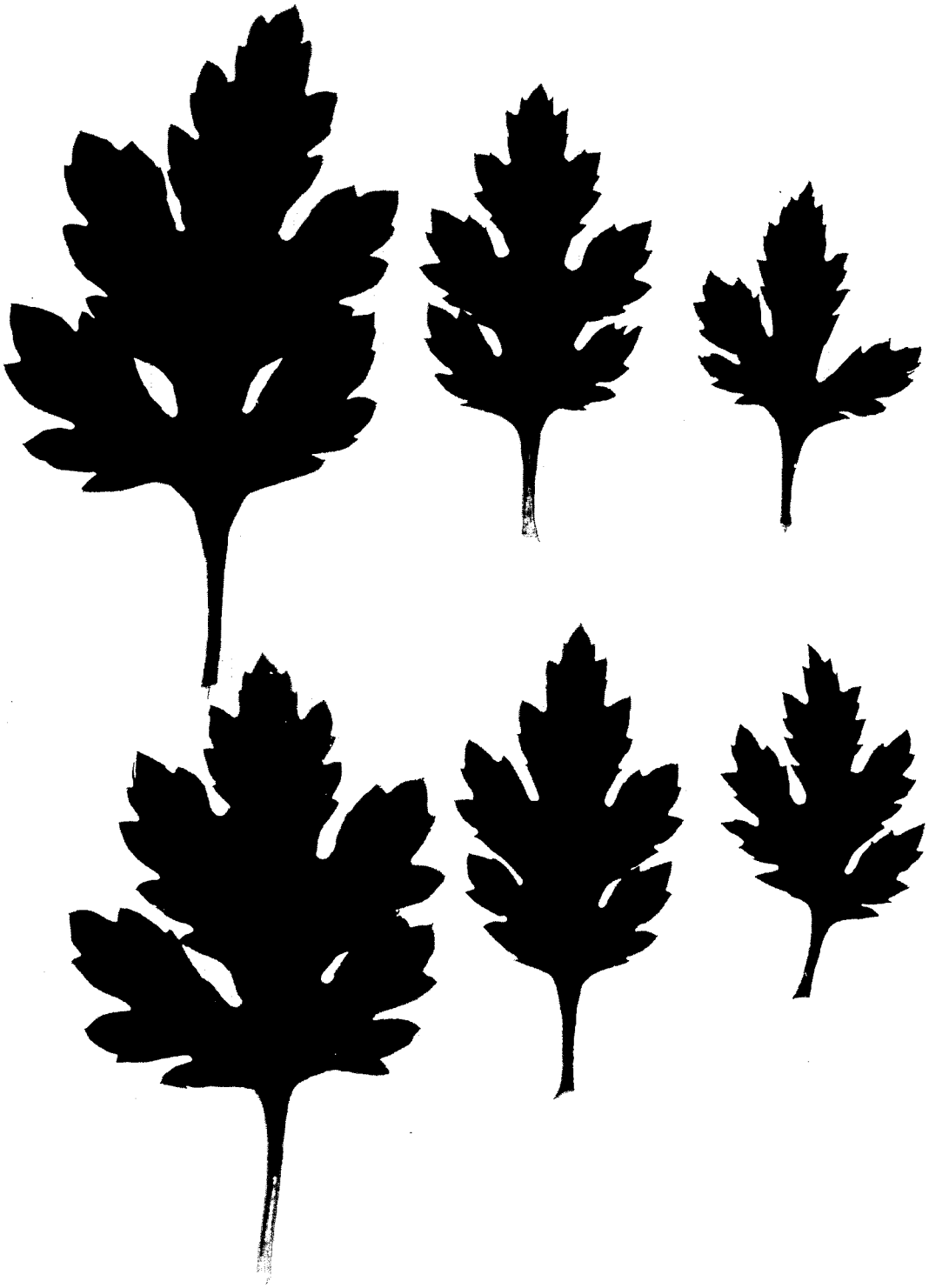

UNITED STATES PATENT AND TRADEMARK OFFICE

CERTIFICATE OF CORRECTION

PATENT NO. : Plant 5,502

DATED : June 25, 1985

INVENTOR(S) : William E. Duffett

It is certified that error appears in the above-identified patent and that said Letters Patent is hereby corrected as shown below:

Column 2, line 19, change "isbudded" to --disbudded--.

Column 3, line 34, change "158B" to --148B--.

Signed and Sealed this

Twenty-eighth Day of October, 1986

[SEAL]

*Attest:*

DONALD J. QUIGG

*Attesting Officer*

*Commissioner of Patents and Trademarks*